(12) United States Patent
Tanaka et al.

(10) Patent No.: US 11,583,166 B2
(45) Date of Patent: Feb. 21, 2023

(54) ANTI-FOGGING HANDHELD IMAGE CAPTURING DEVICE

(71) Applicant: J. MORITA MFG. CORP., Kyoto (JP)

(72) Inventors: Tsuyoshi Tanaka, Kyoto (JP); Naonori Wakazome, Kyoto (JP); Mikinori Nishimura, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 742 days.

(21) Appl. No.: 16/556,341

(22) Filed: Aug. 30, 2019

(65) Prior Publication Data

US 2020/0069169 A1 Mar. 5, 2020

(30) Foreign Application Priority Data

Aug. 31, 2018 (JP) .............................. JP2018-162937

(51) Int. Cl.
*A61B 1/253* (2006.01)
*A61B 1/00* (2006.01)
(Continued)

(52) U.S. Cl.
CPC ...... *A61B 1/00096* (2013.01); *A61B 1/00163* (2013.01); *A61B 1/00194* (2022.02);
(Continued)

(58) Field of Classification Search
CPC ............ A61B 1/00096; A61B 1/00119; A61B 1/00163; A61B 1/00194; A61B 1/04;
(Continued)

(56) References Cited

U.S. PATENT DOCUMENTS

| 7,255,558 B2 * | 8/2007 | Babayoff | ............. | A61C 17/022 |
| | | | | 433/29 |
| 7,946,846 B2 * | 5/2011 | Babayoff | ............... | A61C 9/006 |
| | | | | 433/29 |

(Continued)

FOREIGN PATENT DOCUMENTS

| CN | 201123808 Y | 10/2008 |
| CN | 203841671 U | 9/2014 |

(Continued)

OTHER PUBLICATIONS

Office Action issued in the counterpart Chinese Patent Application No. 201910816657.8, dated Dec. 29, 2020 (12 pages).

(Continued)

*Primary Examiner* — Md N Haque
(74) *Attorney, Agent, or Firm* — Osha Bergman Watanabe & Burton LLP

(57) ABSTRACT

The present disclosure relates to an image capturing device configured to capture an image of a target. The image capturing device includes a probe and a housing. The probe includes an optical component and is configured to receive light from the target. The housing includes electronic components each configured to process the light received from the probe. Moreover, the housing includes an air sending unit, and a controller configured to control driving of the air sending unit. The air sending unit is provided at a position above the electronic components in the housing when a user (Continued)

holds the housing during utilization of the image capturing device, and is configured to supply air to the optical component provided in the probe.

11 Claims, 11 Drawing Sheets

(51) Int. Cl.
 *A61B 1/12* (2006.01)
 *A61B 1/05* (2006.01)
 *A61C 17/022* (2006.01)
 *A61B 1/04* (2006.01)
(52) U.S. Cl.
 CPC .............. *A61B 1/04* (2013.01); *A61B 1/05* (2013.01); *A61B 1/128* (2013.01); *A61B 1/253* (2013.01); *A61C 17/022* (2013.01)
(58) Field of Classification Search
 CPC ........... A61B 1/05; A61B 1/127; A61B 1/128; A61B 1/253
 See application file for complete search history.

(56) References Cited

U.S. PATENT DOCUMENTS

| | | |
|---|---|---|
| 9,204,804 B2 | 12/2015 | Hollenbeck et al. |
| 9,357,926 B2 | 6/2016 | Hollenbeck et al. |
| 9,937,021 B2 | 4/2018 | Babayoff et al. |
| 2009/0103588 A1 | 4/2009 | Umemura |
| 2013/0253272 A1 | 9/2013 | Takahashi |
| 2014/0041145 A1* | 2/2014 | Matsumoto ............ F24F 1/0011 901/1 |
| 2015/0222856 A1 | 8/2015 | Hasegawa et al. |
| 2016/0256244 A1* | 9/2016 | Babayoff ............... A61B 1/253 |
| 2017/0231733 A1 | 8/2017 | Schmid et al. |
| 2019/0029508 A1 | 1/2019 | Tabata et al. |

FOREIGN PATENT DOCUMENTS

| | | |
|---|---|---|
| CN | 204950879 U | 1/2016 |
| CN | 205568909 U | 9/2016 |
| CN | 106725266 A | 5/2017 |
| CN | 107714228 A | 2/2018 |
| CN | 109431442 A | 3/2019 |
| EP | 1517648 B1 | 7/2014 |
| JP | 2006-010983 A | 1/2006 |
| JP | 2009-28416 A | 2/2009 |
| JP | 2009028416 A * | 2/2009 |
| JP | 4810147 B2 | 11/2011 |
| JP | 2012-028974 A | 2/2012 |
| JP | 2013-188269 A | 9/2013 |
| JP | 2014-046016 A | 3/2014 |
| JP | 6265645 B2 | 1/2018 |
| KR | 101844746 B1 | 4/2018 |
| WO | 2007/145233 A1 | 12/2007 |

OTHER PUBLICATIONS

Extended European Search Report in counterpart European Application No. 19194111.1 dated Nov. 20, 2019 (9 pages).
Office Action issued in the counterpart Japanese Patent Application No. 2018-162937, dated May 25, 2021 (8 pages).

* cited by examiner

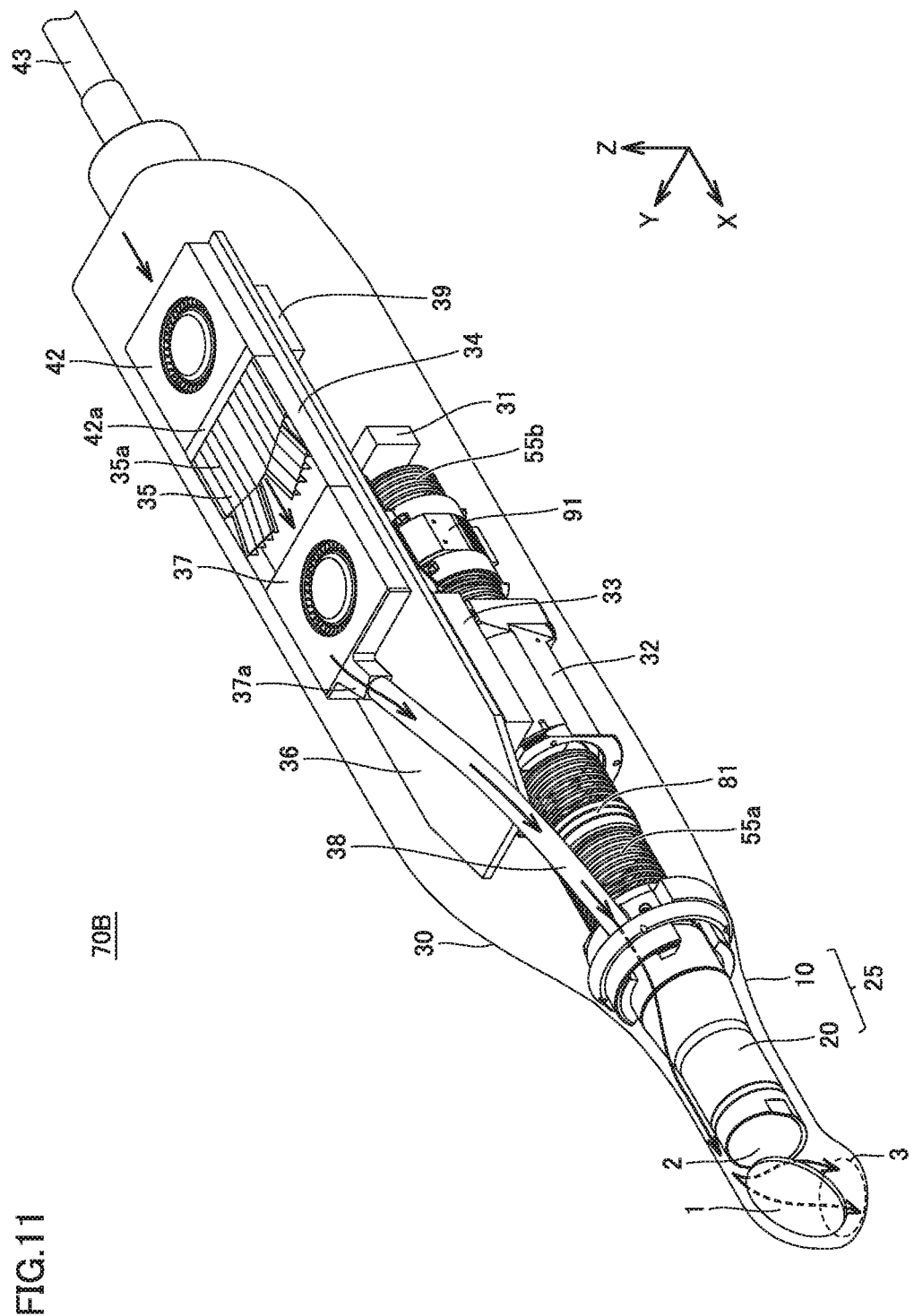

ANTI-FOGGING HANDHELD IMAGE CAPTURING DEVICE

BACKGROUND OF THE INVENTION

Field of the Invention

The present disclosure relates to an image capturing device.

Description of the Background Art

Conventionally, image capturing devices have been used in various fields. For example, in a field of dentistry, various devices have been developed as image capturing devices for capturing images inside an oral cavity. For example, an image capturing device for obtaining a three-dimensional shape of a tooth has been developed in order to digitally design prosthesis or the like on a computer. Such an image capturing device is disclosed in, for example, U.S. Pat. No. 7,255,558 and is referred to as a three-dimensional scanner or an intraoral scanner.

At a tip of the image capturing device, a probe insertable into the oral cavity to capture an image inside the oral cavity may be provided. The probe includes an optical component for guiding light from an observation target to a housing.

When the probe is inserted into the oral cavity so as to capture an image inside the oral cavity, the optical component (for example, a mirror or the like) provided in the probe is fogged due to high temperature and high humidity in the oral cavity. When the optical component provided in the probe is fogged, the image capturing device cannot capture an image inside the oral cavity appropriately.

SUMMARY OF THE INVENTION

In U.S. Pat. No. 7,255,558, warm air is sent to the observation target and a glass surface of the probe in order to remove adhered foreign matters from the observation target and the glass surface of the probe. Hence, U.S. Pat. No. 7,255,558 is not directed to prevention of the fogging of the optical component provided in the probe. Moreover, in U.S. Pat. No. 7,255,558, in order to send the warm air, an air sending unit needs to be provided outside a handpiece, with the result that connection with the handpiece may become complicated.

An object in a certain aspect of the present disclosure is to provide an image capturing device that prevents fogging of an optical component provided in an probe without providing an air sending unit outside a handpiece.

An image capturing device according to an aspect of the present invention is an image capturing device configured to capture an image of a target, the image capturing device including: a probe including an optical component, the probe being configured to receive light from the target; and a housing including electronic components each configured to process the light received from the probe. The housing includes: a first air sending unit configured to supply air to the optical component provided in the probe; and a controller configured to control driving of the first air sending unit. The first air sending unit is provided at a position above the electronic components in the housing when a user holds the housing during utilization of the image capturing device.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 11 shows a configuration of a handpiece according to a third embodiment.

DESCRIPTION OF THE PREFERRED EMBODIMENTS

First Embodiment

A first embodiment will be described with reference to figures. In the first embodiment, the following illustratively describes a three-dimensional scanner 100 that can obtain a three-dimensional shape of a tooth in an oral cavity. It should be noted that such a three-dimensional scanner 100 (intraoral scanner) that can obtain a three-dimensional shape of a tooth in an oral cavity is merely an exemplary implementation of three-dimensional scanner 100 according to the first embodiment, and three-dimensional scanner 100 according to the first embodiment is not limited thereto. Three-dimensional scanner 100 according to the first embodiment may be an image capturing device having a similar configuration, and is applicable to any types of medical practices in not only dentistry but also ophthalmology, otorhinolaryngology, radiology, veterinary medicine, and the like. Moreover, three-dimensional scanner 100 according to the first embodiment may be an image capturing device having a similar configuration and is not limited to medical applications. Moreover, the image capturing device is not limited to three-dimensional scanner 100, and may be an intraoral camera, an optical coherence tomography (OCT), an ultraviolet, infrared, and terahertz imaging device, a fluorescent imaging device, or the like, for example.

[A. Configuration of Three-Dimensional Scanner]

Figure 1:
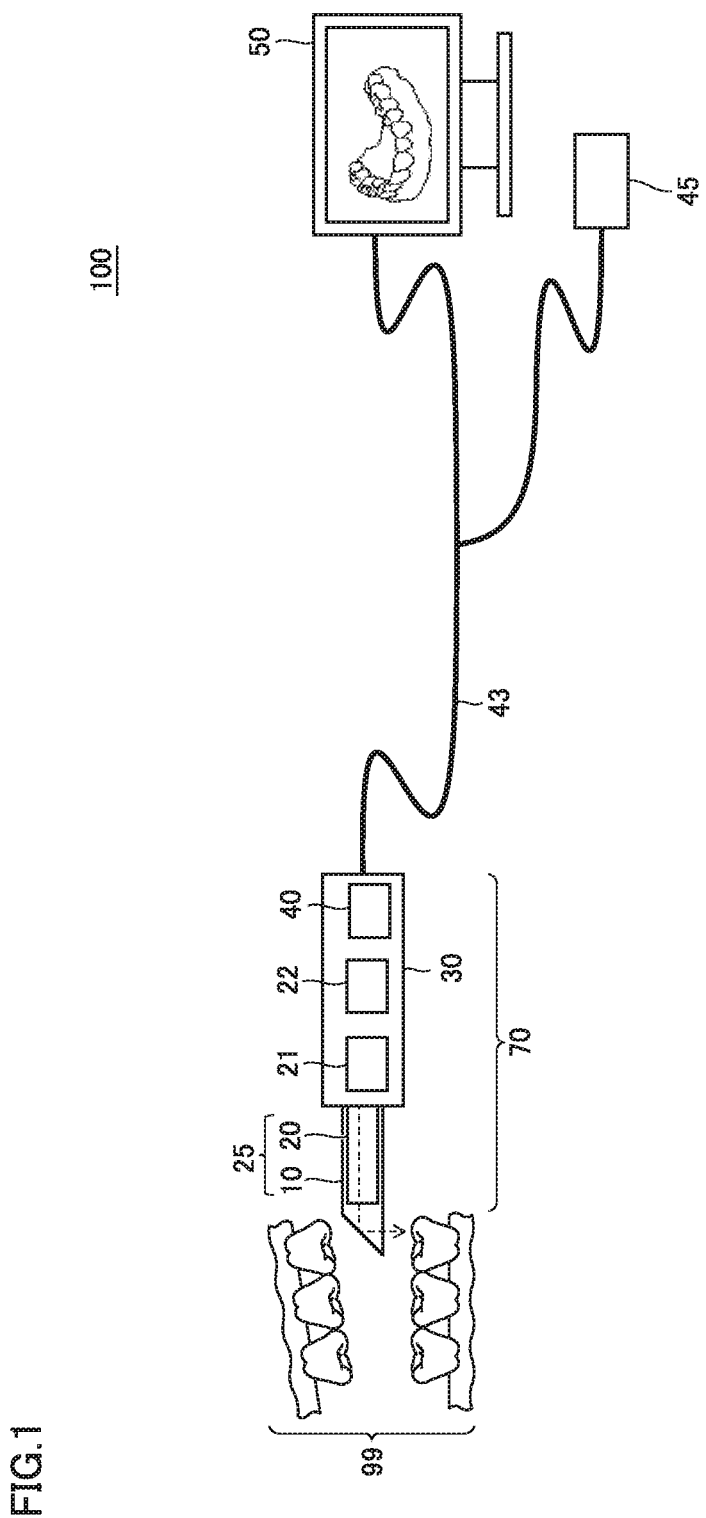
FIG. 1 is a schematic view for illustrating a configuration of a three-dimensional scanner according to a first embodiment.

FIG. 1 is a schematic view for illustrating a configuration of three-dimensional scanner 100 according to the first embodiment. As shown in FIG. 1, three-dimensional scanner 100 includes a handpiece 70, a display unit 50, and a power supply 45, which are connected to one another via a cable 43. Handpiece 70 is a hand-held type member, and includes a probe 25 and a housing 30.

Probe 25 is constituted of a cap 10 and a cylindrical portion 20. Cap 10 is attachable/detachable to/from cylindrical portion 20, and is insertable into an oral cavity in order to obtain a three-dimensional shape by projecting a pattern onto a target 99 such as a tooth. Hence, as a measure against infection, a user can remove only cap 10, which may be brought into contact with a living body, from cylindrical portion 20, and can provide a sterilization treatment (for example, a treatment under a high-temperature and high-humidity environment) thereto. If the sterilization treatment is performed to all the devices of the three-dimensional scanner, the device life may become short because a multiplicity of optical components, electronic components, and the like are included therein. However, when the sterilization treatment is performed only to cap 10 having been removed as described above, the device life can be prevented from being short as much as possible.

Cylindrical portion 20 includes optical components, such as a relay lens and a λ/4 plate, each for guiding light reflected by the target into housing 30. It should be noted that cylindrical portion 20 may be a portion of housing 30 or may be a configuration different from housing 30. In the description below, cylindrical portion 20 is assumed as a portion of housing 30.

Housing 30 includes an image capturing unit 21, an air sending unit 22, and a controller 40.

Image capturing unit 21 projects a pattern onto target 99 and captures an image of the projected pattern. It should be noted that image capturing unit 21 according to the first embodiment is configured to obtain a three-dimensional shape using a principle of the focusing method as described below, but may be configured to obtain a three-dimensional shape using a principle of the confocal method or the like. That is, image capturing unit 21 may be configured to use any of the principles as long as image capturing unit 21 includes a configuration for changing the projected pattern or the focal position of the optical sensor and obtains a three-dimensional shape using an optical method.

Air sending unit 22 controls flow of air in housing 30 and sends air to the tip of probe 25 to prevent fogging of an optical component provided in probe 25. Further, air sending unit 22 is provided at a position above electronic components in housing 30 when a user holds housing 30, whereby the air, which is warmed by heat generated by each of the electronic components and stays at an upper portion of housing 30, is sent to the tip of probe 25. Accordingly, a difference between the surface temperature of the optical component provided in probe 25 and the temperature in the oral cavity is reduced, whereby the fogging of the optical component provided in probe 25 is further prevented.

Controller 40 controls operations of image capturing unit 21, air sending unit 22, and display unit 50. Controller 40 controls the operation of image capturing unit 21 and processes an image captured by image capturing unit 21 so as to obtain a three-dimensional shape. Moreover, controller 40 controls the operation of air sending unit 22 to send the air, warmed by the heat generated by the electronic component, to the tip of probe 25 inserted in the oral cavity. Moreover, controller 40 outputs the obtained three-dimensional shape to display unit 50. Moreover, controller 40 is configured to permit input of setting information of handpiece 70 from an input device (not shown).

Controller 40 includes: a CPU (Central Processing Unit) 34 serving as a control center; a ROM (Read Only Memory) configured to store a program, control data, and the like for operating CPU 34, a RAM (Random Access Memory) serving as a work area of CPU 34; a GPU (Graphics Processing Unit) configured to mainly perform image processing; and an input/output interface for maintaining signal integrity between peripheral devices. It should be noted that the CPU or the GPU may be constituted of an FPGA (Field-Programmable Gate Array).

Display unit 50 presents a measurement result of the three-dimensional shape of target 99 obtained by controller 40. Display unit 50 can present other information such as setting information of handpiece 70, patient information, activation status of the scanner, an instruction manual, and a help screen. For display unit 50, a stationary liquid crystal display, a head-mount type or eye-glasses type wearable display, or the like can be employed, for example. Moreover, a plurality of display units 50 may be provided. The measurement result of the three-dimensional shape and the other information may be presented on the plurality of display units 50 simultaneously or separately.

Power supply 45 supplies electric power to handpiece 70. Power supply 45 may be provided outside handpiece 70 as shown in FIG. 1, but may be provided inside handpiece 70. Moreover, a plurality of power supplies 45 may be provided to individually supply electric power to handpiece 70 and display unit 50.

FIG. 1 illustrates that the components (70, 45, 50) of three-dimensional scanner 100 are connected to one another via cable 43; however, part or whole of the connection may be attained by wireless communication.

[B. Configuration of Handpiece]

Figure 2:
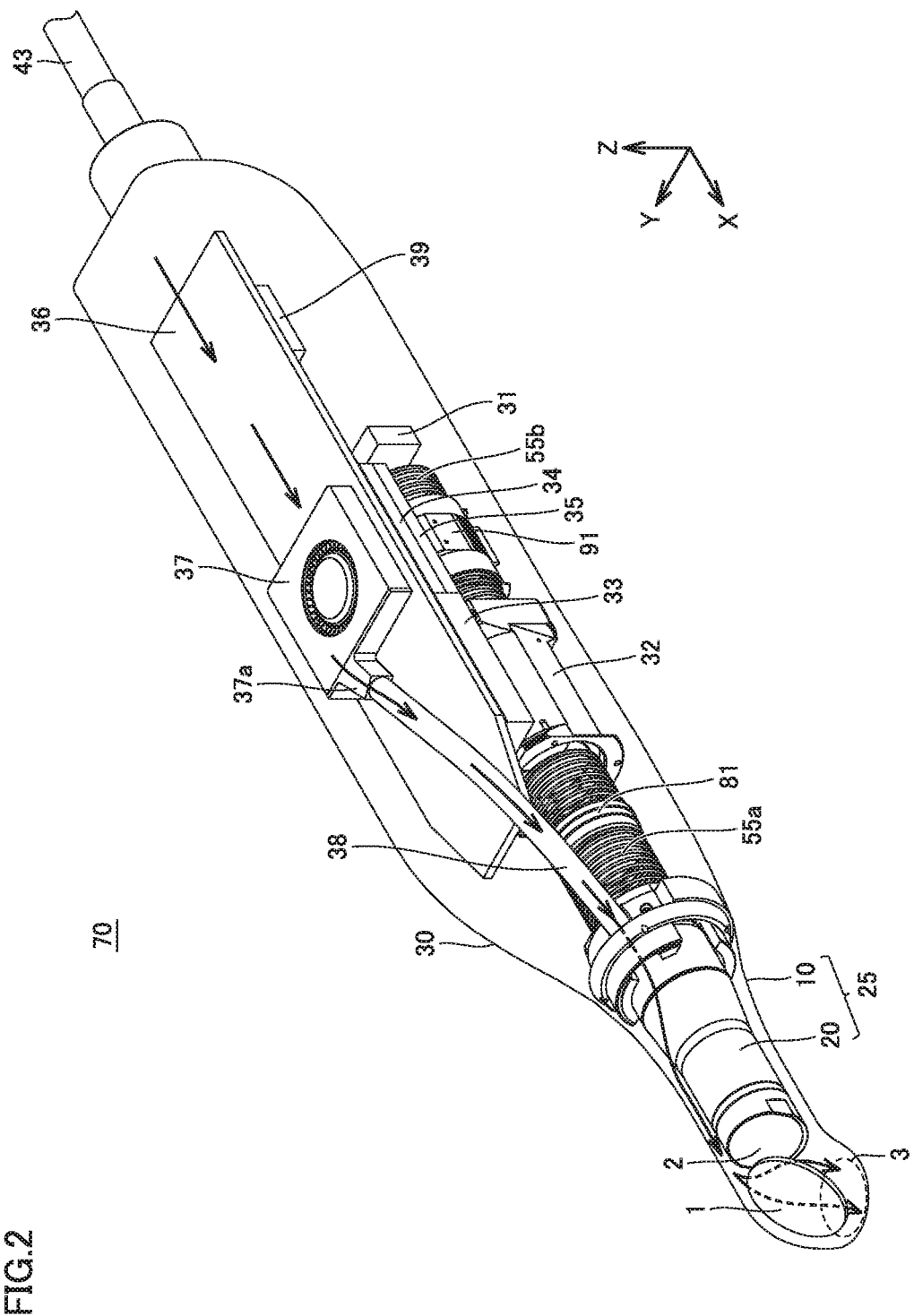
FIG. 2 shows a configuration of a handpiece according to the first embodiment.
Figure 3:
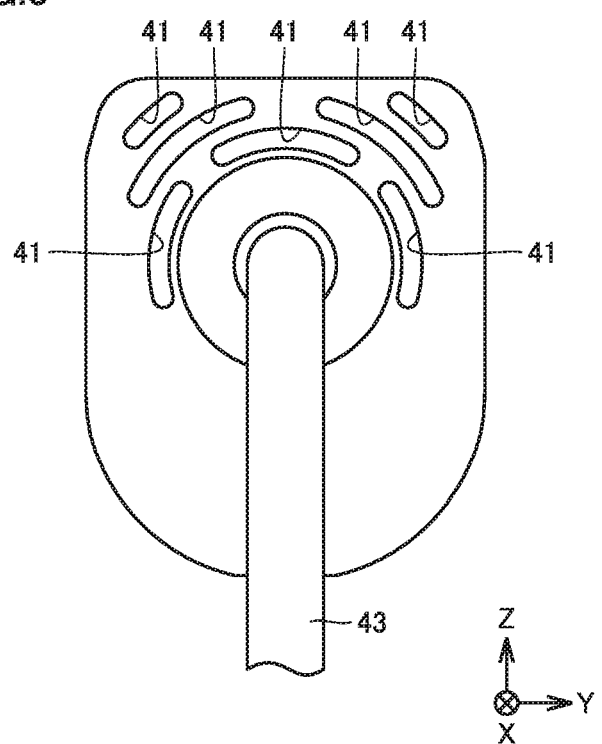
FIG. 3 shows intake ports for outside air in the handpiece according to the first embodiment.

With reference to FIG. 2 and FIG. 3, handpiece 70 according to the first embodiment will be described. FIG. 2 shows a configuration of handpiece 70 according to the first embodiment. FIG. 3 shows intake ports 41 for outside air in handpiece 70 according to the first embodiment. It should be noted that for ease of description, the X axis represents the longitudinal direction of handpiece 70, the Y axis represents the width direction of handpiece 70, and the Z axis represents the height direction of handpiece 70. It should be noted that the X axis direction is parallel to the optical axis of a lens 81 described later.

As shown in FIG. 2, handpiece 70 is constituted of probe 25 and housing 30, and is connected to power supply 45 and display unit 50 via cable 43. Housing 30 is provided with intake ports 41 as shown in FIG. 3 to receive outside air. It should be noted that any types of intake ports 41 may be employed as long as the outside air can be received. The shapes and number of intake ports 41 are not limited to those shown in FIG. 3.

Handpiece 70 shown in FIG. 2 is such a type (pen type) of handpiece that the user holds a portion of housing 30 from above (upper side in the figure) or below (lower side in the figure) for the purpose of operations. The user holds housing 30 itself and inserts the tip of probe 25 into the oral cavity to measure the shape of target 99. Handpiece 70 may be configured to have a lower width smaller than its upper width in consideration of ease of holding and operability for the user.

[C. Probe]

Probe 25 is constituted of cap 10 and cylindrical portion 20. Cap 10 is constituted of a mirror 1 and a cover member that holds mirror 1 and covers cylindrical portion 20. A lighting portion 3 is provided at the tip of cap 10 provided with mirror 1. Lighting portion 3 is a window for projecting light from light source 31 onto target 99, and is also a window for receiving light reflected by target 99. Mirror 1 reflects the light from light source 31 to target 99, and reflects, to housing 30, the light received via lighting portion 3.

Cap 10 is attachable/detachable to/from cylindrical portion 20, and covers at least a portion of cylindrical portion 20. Specifically, cylindrical portion 20 protrudes from housing 30, and cap 10 is configured to engage with a portion of cylindrical portion 20. Although it has been described that cap 10 is attachable/detachable to/from cylindrical portion 20, the configuration is not limited to this and the following configurations and the like may be employed: a configuration in which cap 10 is fixed to cylindrical portion 20; and a configuration in which cylindrical portion 20 and cap 10 are in one piece and are inseparable to constitute one probe 25.

[D. Housing]

Housing 30 includes a multiplicity of electronic components, each of which is mounted on an electronic substrate 36. Examples of the electronic components include: CPU 34 serving as controller 40; image sensor 33 serving as image capturing unit 21; the GPU (not shown); power supply circuit 39; other electronic components (not shown); and the like. Among the electronic components, CPU 34, image sensor 33, the GPU (not shown), and power supply circuit 39 generate larger amounts of heat than those of the other electronic components. Among these, CPU 34 and the GPU (not shown) are arithmetic electronic components that generate particularly large amounts of heat. Hence, a heat sink 35 for releasing the heat is provided at CPU 34.

[E. Air Sending Unit]

Housing 30 includes a first fan 37 serving as air sending unit 22, and an air sending pipe 38. First fan 37 is provided at a position above the electronic components when the user holds housing 30. For example, in FIG. 2, first fan 37 is provided at a position above CPU 34, image sensor 33, the GPU (not shown), power supply circuit 39 and the like in the figure. Air received via intake ports 41 is warmed by heat generated by the electronic components, and stays at an upper portion in housing 30. The warmed air is received by first fan 37 as indicated by arrows of FIG. 2, and is sent to the tip of probe 25 through air sending pipe 38 connected to an air outlet 37a provided in first fan 37. In probe 25, the air passes through an air sending path constituted of cap 10 and the portion of cylindrical portion 20 covered with cap 10.

When probe 25 is inserted into an oral cavity, each of the optical components (for example, mirror 1, a phase difference plate 2 (λ/4 plate) provided in cylindrical portion 20, and the like) provided in probe 25 is fogged due to high temperature and high humidity in the oral cavity, with the result that the shape of target 99 cannot be precisely measured. However, three-dimensional scanner 100 according to the first embodiment sends the air to the tip of probe 25 by first fan 37, thereby preventing the fogging of the optical component provided in probe 25. Particularly, by sending the warm air to the tip of probe 25, a difference between the surface temperature of the optical component provided in probe 25 and the temperature in the oral cavity is reduced, whereby the fogging can be further prevented.

[F. Image Capturing Unit]

As image capturing unit 21, housing 30 includes a light source 31, a prism 32, a lens 81, and an image sensor 33. Moreover, cylindrical portion 20 includes the optical components for guiding light received by probe 25 to housing 30, such as a lens system (not shown), a cover glass (not shown), an optical filter (not shown), and phase difference plate 2 (λ/4 plate).

The light output from light source 31 passes through prism 32 and lens 81, and is projected toward target 99 by mirror 1. The light reflected by target 99 is received by probe 25 via lighting portion 3, and is guided to cylindrical portion 20 by mirror 1. The light guided to cylindrical portion 20 passes through phase difference plate 2, lens 81, and prism 32, and is detected by image sensor 33. When obtaining the three-dimensional shape using the technique of the focusing method, the light having passed through a pattern generation element (not shown) provided between lens 81 and target 99 is projected onto target 99. When lens 81 is reciprocated linearly in the X axis direction, the focal position of the projected pattern is changed. Whenever such a change is made, image sensor 33 detects light from target 99. Based on the position of lens 81 and the detection result provided by image sensor 33 at that time, controller 40 calculates shape information of target 99.

When lens 81 fixed by spring 55a is reciprocated linearly in the X axis direction, the position of the center of gravity of handpiece 70 is moved by a mass of lens 81. Resulting vibration is conducted to the hand of the user holding handpiece 70. In order to cancel the vibration, a counter weight 91 is further provided in housing 30. Counter weight 91 is fixed by a spring 55b, and is provided in the direction in which lens 81 is linearly moved, so as not to block a light path between target 99 and lens 81 and a light path between lens 81 and image sensor 33.

[G. First Fan]

First fan 37 will be described with reference to FIG. 4A, FIG. 4B, FIG. 5A, and FIG. 5B. First fan 37 is a blower fan that is less likely to be damaged by pressure and is suitable for sending air into a narrow pipe path. The blower fan can receive air in the direction of rotation shaft 37e and send the air in a direction orthogonal to rotation shaft 37e. It should be noted that first fan 37 may be any fan as long as it is less likely to be damaged by pressure and is suitable for sending air into a narrow pipe path. Examples of first fan 37 may include a diaphragm pump, a PZT micro blower, and the like.

Figure 4A:
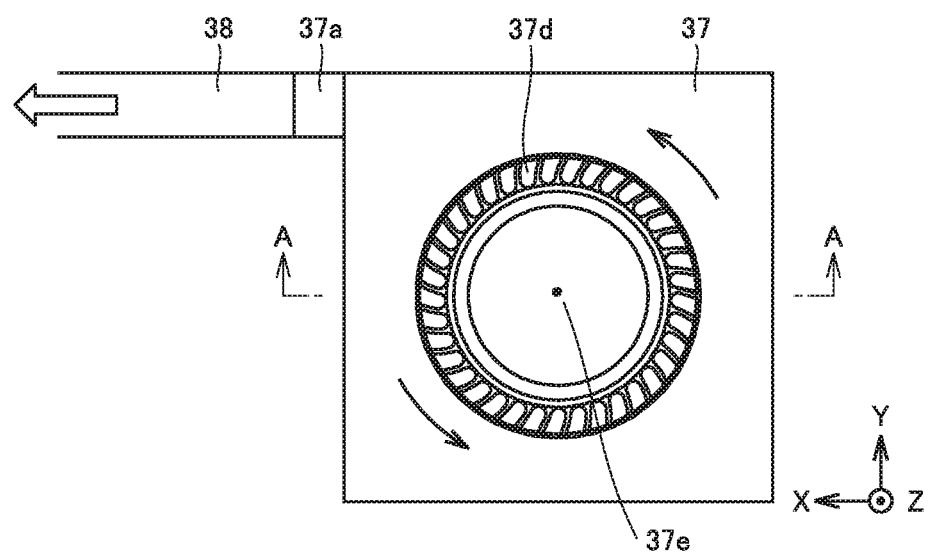
FIG. 4A shows an X-Y cross section of a first fan according to the first embodiment.
Figure 4B:
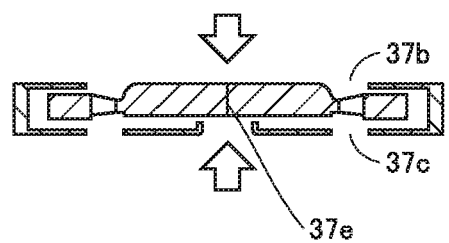
FIG. 4B is a cross sectional view of the first fan taken along a line A-A according to the first embodiment.

First, the following describes a structure of first fan 37 with reference to FIG. 4A and FIG. 4B. FIG. 4A shows an X-Y cross section of first fan 37 according to the first embodiment. FIG. 4B is a cross sectional view of first fan 37 taken along a line A-A according to the first embodiment. White arrows shown in FIG. 4A and FIG. 4B indicate flow of air.

As shown in FIG. 4A and FIG. 4B, first fan 37 is provided with air outlet 37a, air inlets 37b, 37c, rotation blades 37d, and rotation shaft 37e The plurality of rotation blades 37d are radially fixed to rotation shaft 37e. Arrows illustrated in first fan 37 indicate a rotation direction of rotation blades 37d. In FIG. 4A, rotation blades 37d are rotated counter clockwise, but may be rotated clockwise. The rotation direction, number of rotations, rotation speed and the like of rotation blades 37d are controlled by controller 40.

As shown in FIG. 4B, air inlets 37b, 37c are provided in the direction of rotation shaft 37e, and air in housing 30 is received via air inlets 37b, 37c. Moreover, as shown in FIG. 4A, air outlet 37a is provided in the direction orthogonal to rotation shaft 37e, and the air received via air inlets 37b, 37c is sent from air outlet 37a. Air outlet 37a is provided in the direction of probe 25 and is connected to air sending pipe 38 that extends to the root of probe 25. Air sending pipe 38 may be soft (such as silicon, urethane, or polytetrafluoroethylene)

or may be hard (stainless steel, aluminum, or copper). The air sent from air outlet 37a is sent to the root of probe 25 through air sending pipe 38, and is then sent to the tip of probe 25 via an air sending path (not shown) formed between probe 25 and housing 30.

As shown in FIG. 2, FIG. 4A, and FIG. 4B, each of air inlets 37b, 37c is configured to have a larger area of opening than that of air outlet 37a Moreover, air inlet 37b or air inlet 37c is provided at a position facing a specific electronic component that generates a larger amount of heat than those of the other electronic components. For example, in FIG. 2, air inlet 37b or air inlet 37c is provided at a position facing CPU 34.

Thus, air inlets 37b, 37c are provided in the direction of rotation shaft 37e, and air outlet 37a is provided in the direction orthogonal to rotation shaft 37e (in a side surface of first fan 37). Accordingly, air can be sent in the direction orthogonal to the direction in which the air has been received, whereby first fan 37 can be made thin.

Moreover, each of air inlets 37b, 37c is configured to have a larger area of opening than that of air outlet 37a. Accordingly, the air can be efficiently received via air inlets 37b, 37c each having a comparatively large area of opening, and the air can be efficiently sent from air outlet 37a having a comparatively small area of opening.

Moreover, air outlet 37a is provided in the direction of probe 25, and is connected to air sending pipe 38 extending to the root of probe 25. With such connection of first fan 37 and air sending pipe 38, the air can be sent in an intended direction efficiently while minimizing a space therefor.

Moreover, first fan 37 may have a cascade structure. Accordingly, a discharge pressure is increased, whereby the air can be more strongly sent to the tip of probe 25.

Moreover, although first fan 37 is in contact with electronic substrate 36 in FIG. 2, the configuration is not limited to this. First fan 37 may be supported by a support portion (not shown) or the like, and may not be in contact with electronic substrate 36. When first fan 37 is not in contact with electronic substrate 36, the warmed air can be received via both air inlet 37b and air inlet 37c.

Figure 5A:
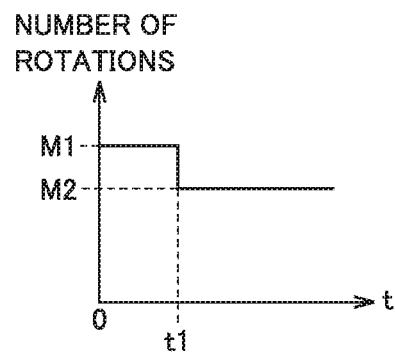
FIG. 5A is a first graph showing the number of rotations of the first fan according to the first embodiment.
Figure 5B:
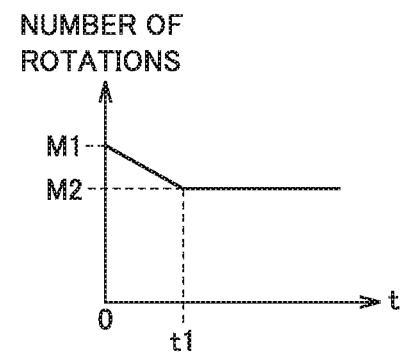
FIG. 5B is a second graph showing the number of rotations of the first fan according to the first embodiment.

Next, with reference to FIG. 5A and FIG. 5B, the following describes the number of rotations of first fan 37. The number of rotations of first fan 37 is controlled by controller 40. FIG. 5A is a first graph showing the number of rotations of first fan 37 according to the first embodiment. FIG. 5B is a second graph showing the number of rotations of first fan 37 according to the first embodiment. In FIG. 5A and FIG. 5B, the horizontal axis represents a passage of time (t seconds) from the start of image capturing, whereas the vertical axis represents the number of rotations (M) of rotation blades 37d of first fan 37.

As shown in FIG. 5A, controller 40 controls such that the number of rotations of rotation blades 37d becomes the maximum value (M1) at the time of start of the image capturing (t=0). At a timing elapsed by a predetermined time (t1), controller 40 changes the number of rotations of rotation blades 37d to M2 that is less than M1, and then maintains the changed number of rotations (M2).

On the other hand, controller 40 may perform control as shown in FIG. 5B. That is, in the same manner as in FIG. 5A, controller 40 controls such that the number of rotations of rotation blades 37d becomes the maximum value (M1) at the time of start of the image capturing (t=0). Then, controller 40 decreases the number of rotations of rotation blades 37d at a predetermined rate. Controller 40 controls such that after passage of the predetermined time (t1), the number of rotations of rotation blades 37d becomes a certain value (M2).

As shown in FIG. 5A and FIG. 5B, controller 40 controls such that the number of rotations of rotation blades 37d becomes the maximum at the time of start of the image capturing. Accordingly, even at the time of start of the image capturing at which the amount of heat generated by the electronic components is small, the amount of air sent to the tip of probe 25 can be increased.

Moreover, as shown in FIG. 5A, after the passage of the predetermined time (t1) from the start of the image capturing, the number of rotations of rotation blades 37d is decreased to be smaller than that at the time of start of the image capturing, and then the number of rotations (M2) is maintained. Accordingly, energy saving is achieved. It should be noted that after the passage of the predetermined time (t1) from the start of the image capturing, temperature increase of the air due to the generation of heat by the electronic components can be sufficiently expected even when the amount of the air sent to the tip of probe 25 is decreased. Thus, the fogging of the optical component provided in probe 25 can be prevented.

Moreover, as shown in FIG. 5B, after the start of the image capturing, the number of rotations of rotation blades 37d is decreased at the predetermined rate. After reaching the certain number of rotations (M2), the number of rotations is maintained. Accordingly, energy saving is achieved. It should be noted that even when the amount of the air sent to the tip of probe 25 is decreased, the amount of heat generated by the electronic component is increased gradually after the start of the image capturing. Hence, temperature increase of the air due to the heat generated by the electronic component can be expected, whereby the fogging of the optical component provided in probe 25 can be prevented.

[H. Linear Motions of Lens and Counter Weight]

Figure 6:
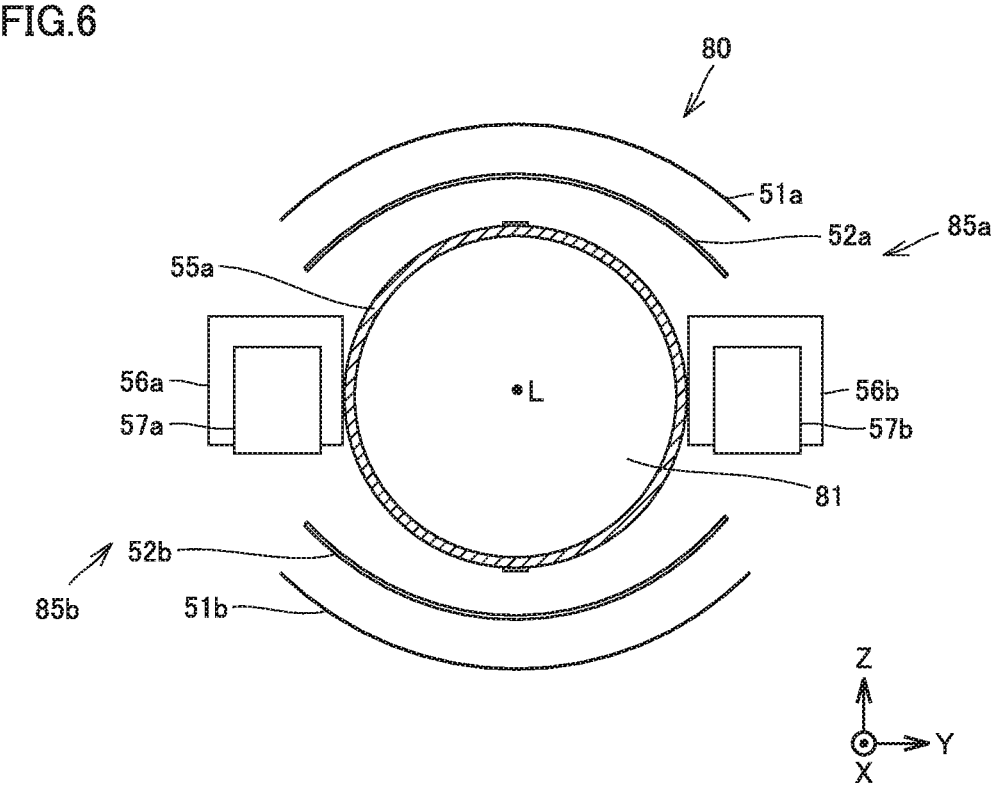
FIG. 6 shows a Y-Z cross section of a first driving unit according to the first embodiment.
Figure 7:
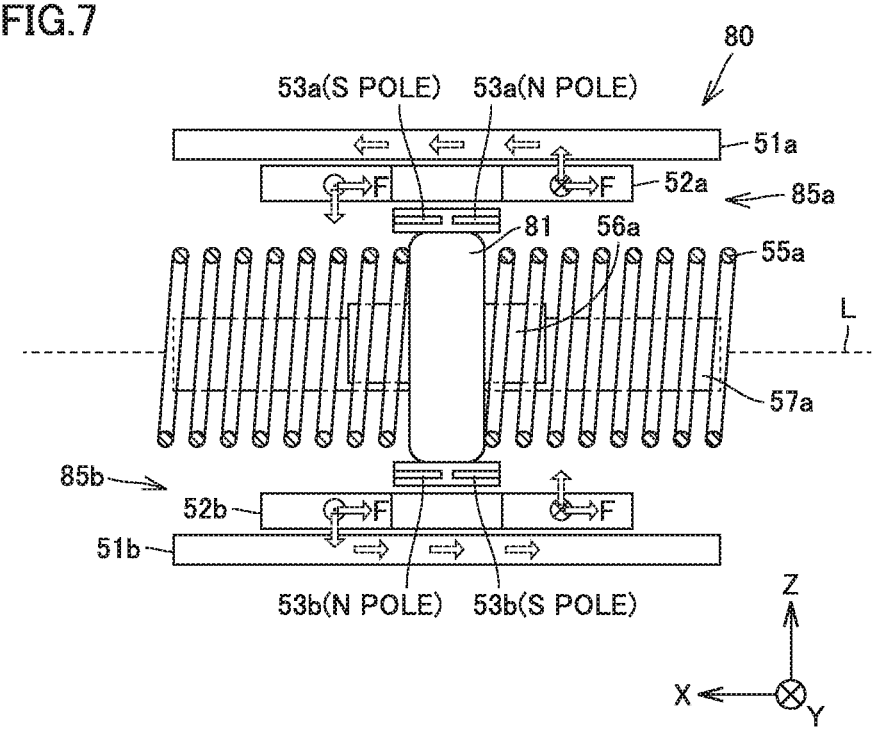
FIG. 7 shows an X-Z cross section of the first driving unit according to the first embodiment.

Next, with reference to FIG. 6 and FIG. 7, the following describes a manner in which lens 81 and counter weight 91 are reciprocated linearly in image capturing unit 21 according to the first embodiment. Lens 81 is reciprocated linearly by a first driving unit 80, and counter weight 91 is reciprocated linearly by a second driving unit (not shown). FIG. 6 shows a Y-Z cross section of first driving unit 80 according to the first embodiment. FIG. 7 shows an X-Z cross section of first driving unit 80 according to the first embodiment.

As shown in FIG. 6, first driving unit 80 has a hollow elongated shape along a linear motion direction (hereinafter, also referred to as "straight line L") such that lens 81 having a substantially circular shape can be provided at the central portion thereof and each member for linearly reciprocating lens 81 is provided around lens 81. Since lens 81 having the substantially circular shape is thus provided at the central portion of first driving unit 80, light can be supplied to the central portion of first driving unit 80.

Specifically, as shown in FIG. 6, in first driving unit 80, a support portion constituted of a fixed support portion 57a and a movable support portion 56a, and a support portion constituted of a fixed support portion 57b and a movable support portion 56b are provided at the outer peripheral portion of lens 81. Movable support portion 56a and movable support portion 56b linearly reciprocates lens 81 along fixed support portion 57a and fixed support portion 57b.

Further, as shown in FIG. 7, spring 55a having an elongated shape is provided at the outer periphery of lens 81 to surround the outer periphery of lens 81 so as not to block a light path at the central portion of lens 81. In a longitudinal cross section of first driving unit 80, spring 55a is disposed to sandwich lens 81 in the direction of straight line L. The diameter of spring 55a may be substantially the same as the diameter of lens 81 such that lens 81 can be fixed. Spring 55a is an elastic member, and is held in the housing such that spring 55a is permitted to be deformed in the X direction and is avoided from being deformed in the Y-Z direction. With spring 55a thus disposed, lens 81 is fed with elastic force in the linear motion direction.

At an outer side relative to spring 55a (direction to separate away from the center of lens 81), magnetic circuit configurations 85a, 85b are provided to reciprocate lens 81 linearly in the direction of straight line L. Magnetic circuit configurations 85a, 85b respectively include: magnets 53a, 53b constituted of the N pole and the S pole; and coils 52a, 52b disposed at outer sides relative to magnets 53a, 53b.

For example, by respectively disposing magnet 53a and magnet 53b constituted of the N pole and the S pole in such a positional relation as shown in FIG. 7 in magnetic circuit configuration 85a and magnetic circuit configuration 85b, a magnetic field in a direction of arrow indicated by a dotted line is generated. In this case, when currents as shown in FIG. 7 ("x" represents a current flowing along the Y axis from the foreside to the rear side in the figure, and "•" represents a current flowing along the Y axis from the rear side to the foreside in the figure) respectively flow in coil 52a and coil 52b, electromagnetic force (F) is generated in the X axis direction as indicated by solid line arrows in accordance with the Fleming's left hand rule. The generated electromagnetic force (F) is exerted onto magnet 53a and magnet 53b serving as movable elements, with the result that magnet 53a and magnet 53b are moved in a direction opposite to the electromagnetic force (F). Hereinafter, configurations related to motion of an object within the device will be referred to as "motion system". Examples of the configurations include spring 55a, magnets 53a, 53b, lens 81, coils 52a, 52b, a damper including lubricant having viscosity such as grease, and the like.

Lens 81 is vibrated in the direction of straight line L due to force of the motion system such as inertia force of lens 81, the electromagnetic force (F), elastic force of spring 55a, and viscous force of the damper. By using this vibration, controller 40 reciprocates lens 81 linearly in the direction of straight line L. That is, controller 40 controls first driving unit 80 at a certain cycle in accordance with the natural vibration frequency of the motion system to supply currents to magnetic circuit configuration 85a and magnetic circuit configuration 85b, whereby lens 81 can be linearly reciprocated in the direction of straight line L using a resonance phenomenon by the motion system. It should be noted that counter weight 91 is linearly reciprocated by the second driving unit in the same manner as the linear reciprocation of lens 81.

When lens 81 is reciprocated linearly in the direction of straight line L by first driving unit 80, counter weight 91 is reciprocated linearly by the second driving unit in a direction opposite to lens 81 by the same distance as the distance in which lens 81 is reciprocated linearly. For example, when lens 81 is moved on straight line L by 10 mm in a direction to approach target 99, counter weight 91 is moved on straight line L by 10 mm in a direction to separate away from target 99. On the other hand, when lens 81 is moved on straight line L by 15 mm in the direction to separate away from target 99, counter weight 91 is moved on straight line L by 15 mm in the direction to approach target 99.

Controller 40 independently controls: first driving unit 80 configured to reciprocate lens 81 linearly; and the second driving unit configured to reciprocate counter weight 91 linearly. Accordingly, the vibration resulting from the linear reciprocation of lens 81 can be canceled by counter weight 91 while changing the focal position of the projected pattern on target 99.

[I. Another Implementation of Handpiece]

Figure 8:
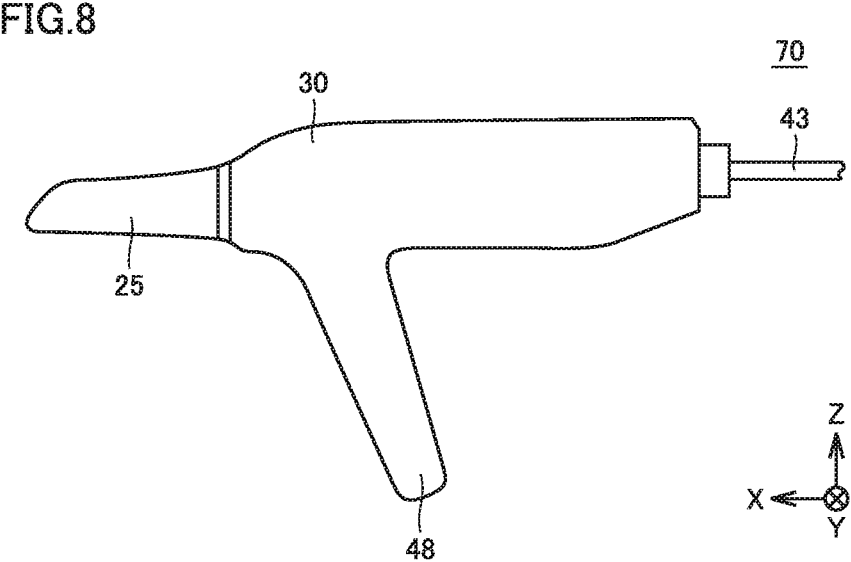
FIG. 8 shows another implementation of the handpiece according to the first embodiment.

FIG. 8 shows another implementation of the handpiece according to the first embodiment. Handpiece 70 may be provided with a handle 48 as shown in FIG. 8. When handle 48 is provided in handpiece 70, the user grabs handle 48 and inserts the tip of probe 25 into the oral cavity to measure the shape of target 99.

[J. Conclusion]

Thus, in three-dimensional scanner 100 according to the first embodiment, air is sent to the tip of probe 25 by first fan 37 provided in housing 30. Accordingly, the fogging of the optical component provided in probe 25 can be prevented without providing an air sending unit outside the handpiece.

Moreover, in three-dimensional scanner 100 according to the first embodiment, first fan 37 is provided at the position above the electronic components in housing 30 when the user holds housing 30. Accordingly, the air warmed by the heat generated by the electronic components is received and sent to the tip of probe 25 by first fan 37. As a result, the difference between the surface temperature of the optical component provided in probe 25 and the temperature in the oral cavity is reduced, whereby the fogging can be further prevented. Moreover, since the air warmed by the heat generated by the electronic components is sent to the tip of probe 25, the electronic components are cooled.

Moreover, in three-dimensional scanner 100 according to the first embodiment, first fan 37 may be provided near a specific electronic component that generates a larger amount of heat than those of the other electronic components. Accordingly, the air warmed further by the specific electronic component that generates a larger amount of heat than those of the other electronic components can be sent to the tip of probe 25, whereby the fogging of the optical component provided in probe 25 is further prevented.

Further, the specific electronic component that generates a larger amount of heat than those of the other electronic components includes at least one of the FPGA, CPU 34, image sensor 33, the GPU, and power supply circuit 39.

Moreover, in three-dimensional scanner 100 according to the first embodiment, each of air inlets 37b, 37c may be provided in the direction of rotation shaft 37e, and air outlet 37a may be provided in the direction orthogonal to rotation shaft 37e. Accordingly, first fan 37 is made thin, thus achieving downsizing of handpiece 70.

Moreover, in three-dimensional scanner 100 according to the first embodiment, each of air inlets 37b, 37c may be configured to have a larger area of opening of than that of air outlet 37a. Accordingly, air can be efficiently received via air inlets 37b, 37c each having a comparatively large area of opening and the air can be efficiently sent to the tip of probe 25 from air outlet 37a having a comparatively small area of opening, whereby the fogging of the optical component provided in probe 25 is further prevented.

Moreover, in three-dimensional scanner 100 according to the first embodiment, air outlet 37a may be provided in the direction of probe 25, and may be connected to air sending pipe 38 extending to the root of probe 25. With such connection, the air can be sent in an intended direction efficiently while minimizing a space therefor.

Moreover, in three-dimensional scanner 100 according to the first embodiment, air inlet 37b or air inlet 37c may be provided at a position facing the specific electronic component that generates a larger amount of heat than those of the other electronic components. Accordingly, the air warmed further by the specific electronic component that generates a larger amount of heat than those of the other electronic components can be sent to the tip of probe 25, whereby the fogging of the optical component provided in probe 25 is further prevented.

Moreover, in three-dimensional scanner 100 according to the first embodiment, controller 40 may control such that the number of rotations of rotation blades 37d becomes the maximum at the time of start of the image capturing. Accordingly, even at the time of start of the image capturing at which the amount of heat generated by the electronic component is small, the amount of air sent to the tip of probe 25 can be increased, whereby the fogging of the optical component provided in probe 25 is prevented.

Moreover, in three-dimensional scanner 100 according to the first embodiment, controller 40 may control such that the number of rotations of rotation blades 37d is decreased at a predetermined rate from the start of the image capturing and the number of rotations is maintained at a certain value after passage of a predetermined time. With such control, energy saving is achieved. Moreover, with such control, the amount of the air sent to the tip of probe 25 is adjusted, thereby avoiding such a situation that the tip of probe 25 has a temperature higher than necessary.

Moreover, in three-dimensional scanner 100 according to the first embodiment, the specific electronic component that generates a larger amount of heat than those of the other electronic components is mounted on electronic substrate 36, and when the user holds housing 30, first fan 37, electronic substrate 36, and image capturing unit 21 are positioned in this order from above in housing 30. Handpiece 70 has a lower width smaller than its upper width in consideration of ease of holding and operability for the user. In a limited space of housing 30, such a configuration ensures a space for electronic substrate 36 on which the specific electronic component that generates a larger amount of heat than those of the other electronic components is mounted. Moreover, due to such a positional relation between first fan 37 and the specific electronic component that generates a larger amount of heat than those of the other electronic components, the air warmed further by the specific electronic component that generates a larger amount of heat than those of the other electronic components is sent to the tip of probe 25, whereby the fogging of the optical component provided in probe 25 is further prevented.

Second Embodiment

Figure 9:
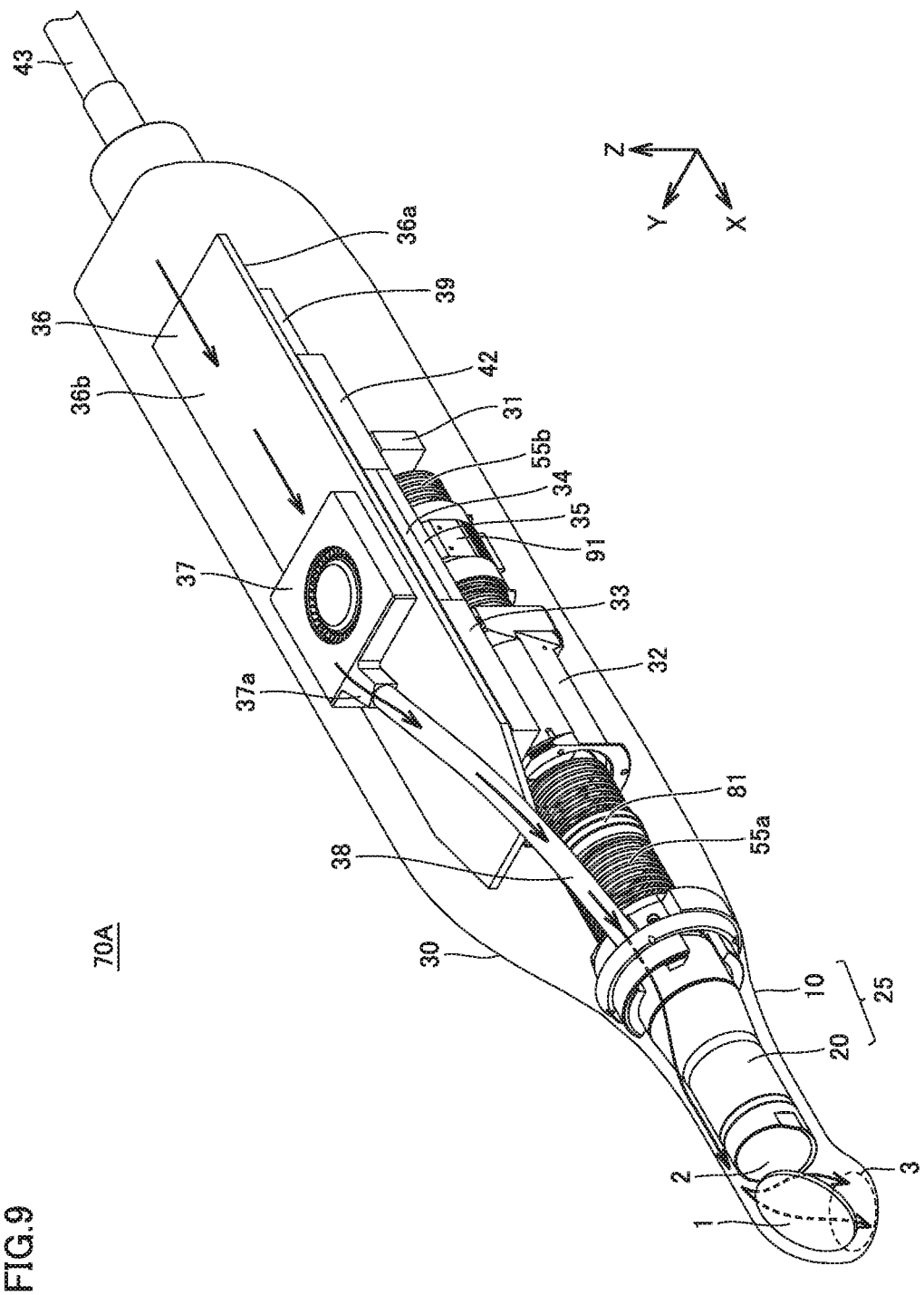
FIG. 9 shows a configuration of a handpiece according to a second embodiment.
Figure 10:
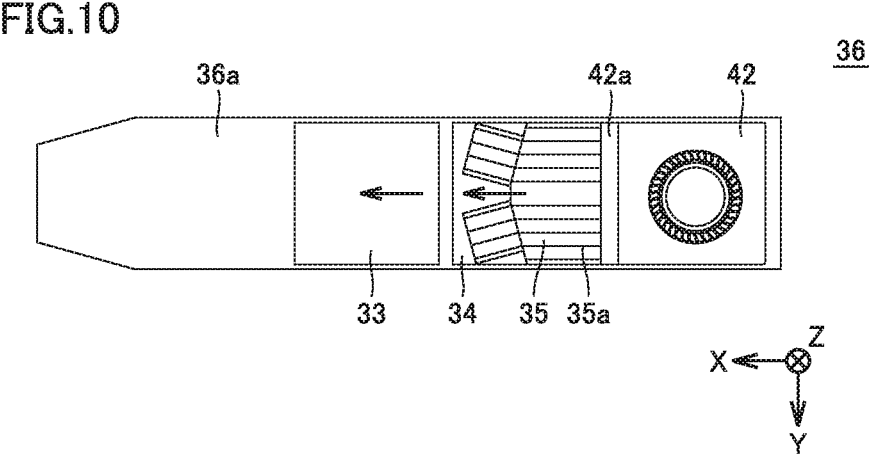
FIG. 10 shows a first substrate surface of an electronic substrate according to the second embodiment.

A three-dimensional scanner 100 according to a second embodiment is different from three-dimensional scanner 100 according to the first embodiment in the following point: not only first fan 37 described in the first embodiment but also a second fan are provided in housing 30. With reference to FIG. 9 and FIG. 10, the following describes three-dimensional scanner 100 according to the second embodiment. It should be noted that since three-dimensional scanner 100 according to the second embodiment is the same as three-dimensional scanner 100 according to the first embodiment except for the above-described point, the same configurations will not be described repeatedly.

FIG. 9 shows a configuration of a handpiece 70A according to the second embodiment. FIG. 10 shows a first substrate surface 36a of an electronic substrate 36 according to the second embodiment. As shown in FIG. 9, not only first fan 37 described in the first embodiment but also a second fan 42 having the same structure as that of first fan 37 are provided in housing 30.

In housing 30, second fan 42 is provided at a side of a substrate surface (hereinafter, also referred to as "first substrate surface 36a") of electronic substrate 36 on which the specific electronic component that generates a larger amount of heat than those of the other electronic components is mounted. For example, in FIG. 9, in housing 30, second fan 42 is provided at the side of first substrate surface 36a of electronic substrate 36 on which CPU 34, image sensor 33, and power supply circuit 39 are mounted. Second fan 42 receives air having a comparatively low temperature and having been received via intake ports 41 and sends the air toward the electronic components mounted on electronic substrate 36. As a result, the electronic components are cooled efficiently.

Moreover, second fan 42 is provided with an air outlet 42a. On first substrate surface 36a, an arithmetic electronic component may be mounted in a direction in which the air sent from air outlet 42a flows. For example, as shown in FIG. 10, CPU 34 is mounted on first substrate surface 36a in the direction in which the air sent from air outlet 42a flows. Moreover, heat sink 35 is provided near CPU 34. Heat sink 35 has a cooling fin 35a in a direction parallel to the direction in which the air is sent from air outlet 42a. Further, on first substrate surface 36a, the other electronic components such as image sensor 33 are provided in a direction in which the air guided by cooling fin 35a flows. Accordingly, the air having a comparatively low temperature and sent from second fan 42 is sent to heat sink 35 provided at CPU 34 that generates a particularly large amount of heat, and a larger amount of heat can be removed by cooling fin 35a, thus resulting in improved cooling efficiency for CPU 34. Moreover, since the air having passed through cooling fin 35a is guided to image sensor 33, image sensor 33 is cooled efficiently.

First fan 37 is provided at a side of a substrate surface (hereinafter, also referred to as "second substrate surface 36b") opposite to first substrate surface 36a in housing 30. For example, in FIG. 9, in housing 30, first fan 37 is provided at the side of second substrate surface 36b opposite to first substrate surface 36a on which CPU 34, image sensor 33, and power supply circuit 39 are mounted. First fan 37 receives the air warmed by heat generated by the electronic components, and sends the air to the tip of probe 25. As a result, the fogging of the optical component provided in probe 25 is further prevented.

Moreover, in housing 30, first fan 37 may be provided near a position of second substrate surface 36b opposite to a position of first substrate surface 36a at which the arithmetic electronic component is mounted. For example, in FIG. 9, in housing 30, first fan 37 is provided near a position of second substrate surface 36b opposite to the position of first substrate 36a at which CPU 34 is mounted. First fan 37 receives the air warmed by heat generated by the electronic component that generates a particularly large amount of heat, and sends the air to the tip of probe 25. As a result, the fogging of the optical component provided in probe 25 is further prevented.

[Conclusion]

In three-dimensional scanner 100 according to the first embodiment, the main purpose of providing first fan 37 is to prevent the fogging of the optical component provided in probe 25. On the other hand, in three-dimensional scanner 100 according to the second embodiment, second fan 42 is provided at the side of first substrate surface 36a on which the specific electronic component that generates a larger amount of heat than those of the other electronic components is mounted, and first fan 37 is provided at the side of second substrate surface 36b opposite to first substrate surface 36a. Accordingly, the air having a comparatively low temperature and received via intake ports 41 is received and sent toward the electronic components mounted on electronic substrate 36 by second fan 42, whereby the electronic components are cooled efficiently. Moreover, the air warmed by the heat generated by the electronic components is received and sent to the tip of probe 25 by first fan 37, whereby the fogging of the optical component provided in probe 25 is further prevented.

Moreover, in three-dimensional scanner 100 according to the second embodiment, in housing 30, first fan 37 may be provided near a position of second substrate surface 36b opposite to the position of first substrate surface 36a at which the arithmetic electronic component is mounted. Accordingly, the air warmed by the heat generated by the electronic component that generates a particularly large amount of heat is received and sent to the tip of probe 25 by first fan 37, whereby the fogging of the optical component provided in probe 25 is further prevented.

Moreover, in three-dimensional scanner 100 according to the second embodiment, the arithmetic electronic component such as CPU 34 may be mounted on electronic substrate 36 in the direction in which the air sent from second fan 42 flows. Moreover, the arithmetic electronic component may be provided with heat sink 35 having cooling fin 35a in the direction parallel to the direction in which second fan 42 sends the air. Further, the other electronic components such as image sensor 33 may be provided on first substrate surface 36a in the direction in which the air guided by cooling fin 35a flows. Accordingly, the air having a comparatively low temperature and sent from second fan 42 is sent to heat sink 35 provided at CPU 34 that generates a particularly larger amount of heat and a larger amount of heat can be removed by cooling fin 35a, thus resulting in improved cooling efficiency for CPU 34. Moreover, since the air having passed through cooling fin 35a is guided to image sensor 33, image sensor 33 is cooled efficiently. It should be noted that cooling fin 35a is also applicable to three-dimensional scanner 100 according to the first embodiment.

Moreover, in three-dimensional scanner 100 according to the second embodiment, second fan 42 is configured to have the same structure as that of first fan 37. Accordingly, second fan 42 is made thin, thus achieving downsizing of handpiece 70. It should be noted that second fan 42 may have a structure different from that of first fan 37.

Third Embodiment

A three-dimensional scanner 100 according to a third embodiment is different from three-dimensional scanner 100 according to the second embodiment in the following points: first fan 37, CPU 34, and second fan 42 are disposed at the side of one substrate surface of electronic substrate 36; and CPU 34 and image sensor 33 are disposed at the side of the other substrate surface of electronic substrate 36. With reference to FIG. 11, the following describes three-dimensional scanner 100 according to the third embodiment. It should be noted that since three-dimensional scanner 100 according to the third embodiment is the same as three-dimensional scanner 100 according to the second embodiment except for the above-described points, the same configurations will not be described repeatedly.

FIG. 11 shows a configuration of a handpiece 70B according to the third embodiment. First fan 37, CPU 34, second fan 42, and intake ports 41 are provided in housing 30 in this order from the side close to probe 25. First fan 37, CPU 34, and second fan 42 are provided at the side of the same substrate surface of electronic substrate 36.

By mounting CPU 34, which generates a particularly large amount of heat, at the side of the substrate surface different from the side of the substrate surface at which the other electronic components such as image sensor 33 are mounted in electronic substrate 36 according to the third embodiment, the locations of the heat generation sources can be divided to the upper and lower sides of the substrate and second fan 42 can be disposed side by side with first fan 37 at the side of the surface at which first fan 37 is mounted. It should be noted that as with the second embodiment, CPU 34 is provided with heat sink 35 having cooling fin 35a in the direction parallel to the direction in which the air is sent via air outlet 42a. With such an arrangement, the air having a comparatively low temperature and received via intake ports 41 is sent by second fan 42 toward the specific electronic component that generates a larger amount of heat than those of the other electronic components, thereby cooling the electronic components. Moreover, with such an arrangement, the air warmed further by the specific electronic component that generates a larger amount of heat than those of the other electronic components is received and sent to the tip of probe 25 by first fan 37, whereby the fogging of the optical component provided in probe 25 is further prevented.

[Conclusion]

Thus, in three-dimensional scanner 100 according to the third embodiment, first fan 37, the specific electronic component that generates a larger amount of heat than those of the other electronic components, second fan 42, and intake ports 41 are provided in this order from the side close to probe 25. CPU 34, which generates a particularly large amount of heat, is mounted at the substrate surface side of electronic substrate 36 different from the substrate surface side of electronic substrate 36 at which the other electronic components such as image sensor 33 are disposed. Moreover, first fan 37 and second fan 42 are disposed at the same substrate surface side of electronic substrate 36. Accordingly, air that changes in temperature can be utilized appropriately. Hence, the electronic components are cooled and the fogging of the optical component provided in probe 25 is prevented. Moreover, since the electronic component that generates a larger amount of heat than those of the other electronic components is provided at the substrate surface side of electronic substrate 36 different from the substrate surface side at which the other electronic components are disposed, the heat is generated from the electronic components in a non-concentrated manner, thus resulting in improved cooling effect.

Although the present invention has been described and illustrated in detail, it is clearly understood that the same is by way of illustration and example only and is not to be taken by way of limitation, the scope of the present invention being interpreted by the terms of the appended claims.

What is claimed is:

1. An image capturing device being handheld and configured to capture an image of a target, the image capturing device comprising:
   a probe including an optical component, the probe being configured to receive light from the target; and
   a housing to be held by a user during utilization of the image capturing device, the housing including electronic components each configured to process the light received from the probe, and an electronic substrate on which the electronic components are mounted, wherein the housing includes a first air sending unit configured to supply air to the optical component provided in the probe, and a controller configured to control driving of the first air sending unit, and the electronic substrate has a first substrate surface and a second substrate surface opposite to the first substrate surface, and a specific electronic component that generates a larger amount of heat than an amount of heat generated by other electronic components in the electronic components is mounted on the first substrate surface, and when a user holds the housing during utilization of the image capturing device, the first air sending unit is provided at a side of the second substrate surface and near the specific electronic component, and when a user holds the housing during utilization of the image capturing device, the first air sending unit, the electronic substrate and the specific electronic component are positioned in this order in the housing, and the first air sending unit is provided with a plurality of rotation blades radially fixed to a rotation shaft, an air inlet via which air is introduced, the air inlet being provided in a direction of the rotation shaft, and an air outlet via which the air introduced via the air inlet is exhausted, the air outlet being provided in a direction orthogonal to the direction of the rotation shaft and in a direction of the optical component, and the air inlet has a larger area of opening than an area of opening of the air outlet.

2. The image capturing device according to claim 1, wherein the specific electronic component includes at least one of an FPGA, a CPU, an image sensor, a GPU, and a power supply circuit.

3. The image capturing device according to claim 1, wherein the air outlet is provided in a direction of the probe, and is connected to an air sending pipe through which the air passes.

4. The image capturing device according to claim 1, wherein the air inlet is provided at a position facing the specific electronic component.

5. The image capturing device according to claim 1, wherein in the housing, a second air sending unit configured to supply air to cool the specific electronic component is provided at a side of the first substrate surface of the electronic substrate.

6. The image capturing device according to claim 5, wherein the first air sending unit is provided near a position of the second substrate surface opposite to a position of the first substrate surface at which an arithmetic component of the specific electronic component is mounted.

7. The image capturing device according to claim 6, wherein the arithmetic component is mounted on the electronic substrate in an exhausting direction in which the air is exhausted by the second air sending unit, and the arithmetic component is provided with a heat sink having a cooling fin in a direction parallel to the exhausting direction.

8. The image capturing device according to claim 5, wherein the first air sending unit, the specific electronic component, the second air sending unit, and an intake port for receiving outside air are provided in the housing in this order from a side close to the probe.

9. The image capturing device according to claim 1, wherein the controller is configured to control such that an amount of driving of the first air sending unit becomes maximum at a time of start of image capturing.

10. The image capturing device according to claim 9, wherein the controller is configured to decrease the amount of driving of the first air sending unit at a predetermined rate from the start of the image capturing, and maintain the amount of driving of the first air sending unit at a certain amount of driving after passage of a predetermined time.

11. The image capturing device according to claim 1, wherein the image capturing device is an intraoral image capturing device.

* * * * *